(12) United States Patent
Fujiwara et al.

(10) Patent No.: US 8,383,531 B2
(45) Date of Patent: *Feb. 26, 2013

(54) GLASS FLAKE

(75) Inventors: Kosuke Fujiwara, Tokyo (JP); Akihiro Koyama, Tokyo (JP)

(73) Assignee: Nippon Sheet Glass Company, Limited, Tokyo (JP)

( * ) Notice: Subject to any disclaimer, the term of this patent is extended or adjusted under 35 U.S.C. 154(b) by 638 days.

This patent is subject to a terminal disclaimer.

(21) Appl. No.: 11/793,787

(22) PCT Filed: Dec. 22, 2005

(86) PCT No.: PCT/JP2005/023681
§ 371 (c)(1),
(2), (4) Date: Jan. 17, 2008

(87) PCT Pub. No.: WO2006/068255
PCT Pub. Date: Jun. 29, 2006

(65) Prior Publication Data
US 2008/0124559 A1    May 29, 2008

(30) Foreign Application Priority Data
Dec. 24, 2004   (JP) ................. 2004-373862

(51) Int. Cl.
*B32B 17/06* (2006.01)
*C03C 3/087* (2006.01)

(52) U.S. Cl. ............. 501/70; 501/30; 501/77; 428/402; 428/403; 428/432

(58) Field of Classification Search ............ 501/30, 501/77
See application file for complete search history.

(56) References Cited

U.S. PATENT DOCUMENTS

| | | | |
|---|---|---|---|
| 4,882,302 A | 11/1989 | Horiuchi et al. | |
| 5,789,329 A | 8/1998 | Eastes et al. | |
| 6,045,914 A * | 4/2000 | Sullivan et al. | 428/404 |
| 6,136,735 A * | 10/2000 | Gallo et al. | 501/36 |
| 6,686,304 B1 * | 2/2004 | Wallenberger | 501/35 |
| 2002/0193233 A1 | 12/2002 | Kishimoto et al. | |
| 2003/0019501 A1 * | 1/2003 | Hirota et al. | 132/73 |
| 2003/0207748 A1 | 11/2003 | Wallenberger | |
| 2003/0224922 A1 * | 12/2003 | Wallenberger | 501/35 |
| 2004/0170838 A1 * | 9/2004 | Ambrosius et al. | 428/406 |
| 2005/0008850 A1 * | 1/2005 | Flynn et al. | 428/331 |
| 2005/0049133 A1 | 3/2005 | Fujiwara et al. | |
| 2006/0241205 A1 * | 10/2006 | Jia | 523/115 |
| 2010/0183737 A1 | 7/2010 | Fujiwara | |

FOREIGN PATENT DOCUMENTS

| | | |
|---|---|---|
| CN | 1243501 A | 2/2000 |
| CN | 1395481 A | 2/2003 |
| EP | 0 165 530 | 12/1985 |
| JP | 61-14152 | 1/1986 |
| JP | 63-20141 | 8/1988 |
| JP | 5-000826 A | 8/1993 |
| JP | 5-306143 | 11/1993 |

(Continued)

*Primary Examiner* — Alicia Chevalier
*Assistant Examiner* — Ronak Patel
(74) *Attorney, Agent, or Firm* — Hamre, Schumann, Mueller & Larson, P.C.

(57) ABSTRACT

A glass flake of the present invention has a composition that includes, in terms of mass %, $59 \leq SiO_2 < 65$, $8 \leq Al_2O_3 \leq 15$, $47 < (SiO_2 - Al_2O_3) \leq 57$, $1 \leq MgO \leq 5$, $20 \leq CaO \leq 30$, $0 < (Li_2O + Na_2O + K_2O) < 2$, and $0 \leq TiO_2 \leq 5$ and that is substantially free from $B_2O_3$, F, ZnO, BaO, SrO, and $ZrO_2$.

18 Claims, 3 Drawing Sheets

FOREIGN PATENT DOCUMENTS

| | | |
|---|---|---|
| JP | 9-143750 | 6/1997 |
| JP | 2001-213639 | 8/2001 |
| JP | 2001-515448 | 9/2001 |
| JP | 2002-348141 | 12/2002 |
| JP | 2003-12962 | 1/2003 |
| JP | 2003-012962 | 1/2003 |
| JP | 2003-500330 | 1/2003 |
| JP | 2003-119690 | 4/2003 |
| JP | 2003-137590 | 5/2003 |
| JP | 2003-246710 | 9/2003 |
| JP | 2004-11036 | 1/2004 |
| JP | 2004-508265 | 3/2004 |
| JP | 2005-506267 | 3/2005 |
| JP | 2005-097080 | 4/2005 |
| WO | WO 96/39362 | 12/1996 |
| WO | WO 00/73231 | 12/2000 |
| WO | WO 02/20419 | 3/2002 |
| WO | 03/033425 | 4/2003 |

\* cited by examiner

GLASS FLAKE

TECHNICAL FIELD

The present invention relates to glass flakes that can be mixed in, for example, resin moldings, coating materials, inks, and cosmetics. Furthermore, the present invention also relates to resin compositions, coating materials, ink compositions, and cosmetics containing the glass flakes.

BACKGROUND ART

Glass flakes allow resin moldings to have improved strength and dimensional accuracy when being dispersed, for example, in a resin matrix. These glass flakes are mixed in coating materials as liners and are then applied to metal or concrete surfaces.

Glass flakes exhibit metallic colors when the surfaces thereof are coated with metal. On the other hand, they exhibit interference colors due to interference of reflected light when the surfaces thereof are coated with metal oxides. That is, a glass flake coated with a coating film formed of metal or metal oxide also can be used as a luster pigment.

Luster pigments produced with glass flakes as described above are commonly used for applications such as coating materials and cosmetics where color tone and luster are considered to be important.

JP 63 (1988)-201041 A describes, as suitable compositions for glass flakes, compositions of C glass produced with chemical durability being considered to be important, E glass developed for electronic products, and sheet glass.

JP 2001-213639 A describes glass flakes with excellent chemical durability. The glass flakes with excellent chemical durability contain neither diboron trioxide ($B_2O_3$) nor fluorine (F), which are volatile components, and the content of alkali metal oxides therein is 5 mass % or lower.

Glass compositions that are not flaky but fibrous with lower contents of alkali metal oxides are disclosed in the following publications:

JP 61 (1986)-14152A: "Glass Fiber"
JP 2001-515448 A: "Boron-Free Glass Fibers"
JP 2003-500330 A: "Glass Fiber Composition"
JP 2004-508265 A: "Glass Fiber Forming Compositions"

Glass flakes can be produced by using an apparatus described, for example, in JP 5 (1993)-826 A. With the apparatus described in the publication, a molten glass base material is blown up into a balloon shape with a blow nozzle to form a hollow glass film, and this hollow glass film is crushed with a pressure roll. Thus glass flakes can be obtained.

DISCLOSURE OF INVENTION

When the production processes as described above are taken into consideration, glass flakes are required to have excellent meltability, a suitable temperature-viscosity property, and a lower devitrification temperature than a working temperature. In this case, the working temperature is a temperature at which glass has a viscosity of 1000 dPa·sec (1000 poise). Furthermore, the devitrification temperature is the temperature at which crystals are formed in the molten glass base material and start to grow. As to the temperature-viscosity property, the working temperature is preferably 1300° C. or lower because an excessively high working temperature particularly makes it difficult to form glass flakes.

Furthermore, when a coating film made of metal or metal oxide is to be formed on the surface of a glass flake, the glass flake may be treated at a high temperature. Moreover, glass flakes or those with a coating film may be mixed in a coating material, which may be used for a baking finish to be treated at a high temperature, for example. Therefore glass flakes also are required to have a sufficiently high heat resistance.

However, soda-lime glass that is used commonly as a so-called sheet glass composition contains a large amount of alkali metal oxides and therefore does not have a sufficiently high heat resistance, which has been a problem.

In the C glass composition and E glass composition among the compositions of the glass flakes described in JP 63 (1988)-201041 A, diboron trioxide ($B_2O_3$) and fluorine (F) are essential components to be contained to adjust the devitrification temperature and viscosity. However, since diboron trioxide ($B_2O_3$) and fluorine (F) tend to volatile, there is a possibility that they disperse during melting. Moreover, there also is a possibility of causing a problem in that, for example, they may erode the wall of a melting furnace or a regenerative furnace to reduce the furnace life.

Furthermore, in all the examples described in JP 2001-213639 A, glasses always contain any one component selected from zinc oxide (ZnO), barium oxide (BaO), strontium oxide (SrO), and zirconium oxide ($ZrO_2$).

However, since the zinc oxide (ZnO) tends to volatile, there is a possibility that it disperses during melting. Furthermore, there is also a problem in that since it volatilizes, the content thereof in the glass is difficult to control.

Generally, the raw materials of barium oxide (BaO) are expensive. Some of them require to be handled with care.

The raw materials of strontium oxide (SrO) are expensive. Since they may contain raw materials of barium oxide (BaO). Therefore some of them require to be handled with care.

The zirconium oxide ($ZrO_2$) increases the devitrification growth rate of glass and thereby often makes it difficult to produce glass flakes stably.

From such reasons as described above, it is desirable not to use diboron trioxide ($B_2O_3$), fluorine (F), zinc oxide (ZnO), barium oxide (BaO), strontium oxide (SrO), and zirconium oxide ($ZrO_2$) in glass flakes.

Moreover, when consideration is given to the fact that the glass flakes are to be mixed in coating materials and cosmetics, they are required to have a high chemical durability.

With these situations in mind, the present invention is intended to provide glass flakes with a glass composition that is substantially free from diboron trioxide ($B_2O_3$), fluorine (F), zinc oxide (ZnO), barium oxide (BaO), strontium oxide (SrO), and zirconium oxide ($ZrO_2$) and that has excellent heat resistance, chemical durability, and formability.

The present inventors devoted themselves to make a series of studies about a glass composition that is suitable for glass flakes and that is substantially free from diboron trioxide ($B_2O_3$), fluorine (F), zinc oxide (ZnO), barium oxide (BaO), strontium oxide (SrO), and zirconium oxide ($ZrO_2$). As a result, they found that when the composition ranges of $SiO_2$ and $Al_2O_3$, and that of ($SiO_2$—$Al_2O_3$), which represents the relationship therebetween, were controlled, the chemical durability (especially acid resistance) was improved considerably and a glass composition that allowed glass flakes to be formed easily could be obtained.

That is, the present invention provides a glass flake having a composition that includes, in terms of mass %:
$59 \leq SiO_2 \leq 65$,
$8 \leq Al_2O_3 \leq 15$,
$47 \leq (SiO_2 - Al_2O_3) \leq 57$,
$1 \leq MgO \leq 5$,
$20 \leq CaO \leq 30$,
$0 < (Li_2O + Na_2O + K_2O) < 2$, and
$0 \leq TiO_2 \leq 5$, and that is substantially free from $B_2O_3$, F, ZnO, BaO, SrO, and $ZrO_2$.

According to the glass flake of the present invention, since it has excellent heat resistance, it is prevented from being deformed when being heated to a high temperature. The glass flake of the present invention is excellent in chemical durability, such as acid resistance, water resistance, and alkali resistance. Particularly, it has excellent acid resistance and therefore can be used as a corrosion-resistant liner in an acid environment. In the above-mentioned composition ranges, since the working temperature can be controlled easily at a relatively low temperature, it is easy to form glass flakes.

Moreover, the present invention provides a glass flake with a coating film that includes the aforementioned glass flake and a coating film. The coating film is composed mainly of metal and/or metal oxide and covers the surface of the glass flake. The glass flake with a coating film can be used as a luster pigment. The term "mainly" denotes that the content of the component is the highest in terms of mass %.

These glass flakes or glass flakes with a coating film can be used in resin compositions, coating materials, ink compositions, and cosmetics by being added thereto.

In the present specification, the glass flake is a flaky particle with an average thickness t of 0.1 μm to 15 μm and an aspect ratio (average particle size a/average thickness t) of 2 to 1000 (see FIG. 2A). In this case, the average particle size a is defined as the square root of the area S of a glass flake viewed in plane (see FIG. 2B).

DESCRIPTION OF THE PREFERRED EMBODIMENTS

[Composition of Glass Flake]

Figure 1:
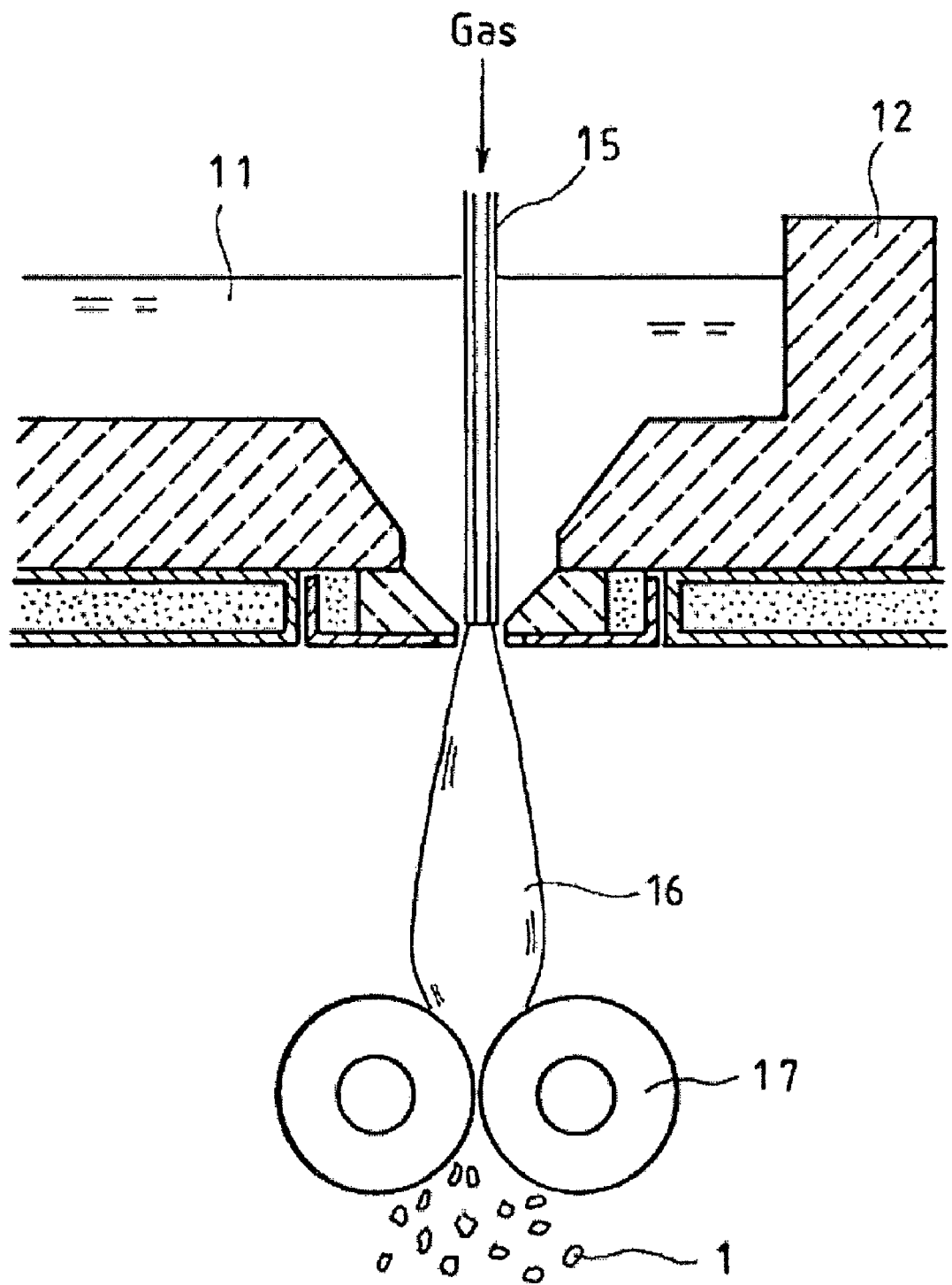
FIG. 1 is a schematic view for explaining an apparatus for producing glass flakes.
Figure 2A:
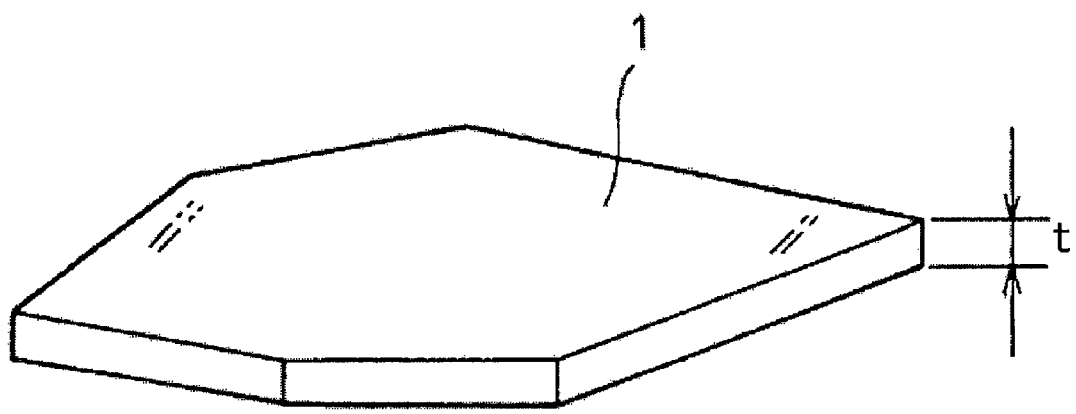
FIG. 2A is a schematic view of a glass flake according to the present invention.
Figure 2B:
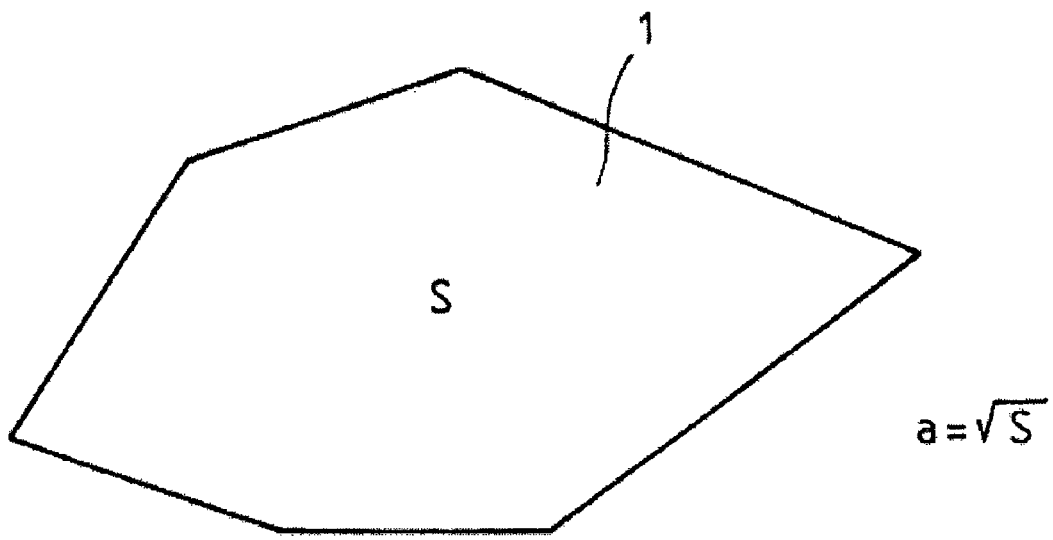
FIG. 2B is a diagram for explaining the method of determining the average particle size.

The composition of the glass flakes of the present invention is described below in detail.

<$SiO_2$>

Silicon dioxide ($SiO_2$) is a main component forming the skeleton of glass. It also adjusts the viscosity and devitrification temperature during glass formation and also improves the acid resistance. When the $SiO_2$ content is lower than 59 mass %, the devitrification temperature becomes excessively high and therefore it becomes difficult to form glass flakes. Furthermore, the acid resistance of glass also is deteriorated. On the other hand, when the $SiO_2$ content exceeds 65 mass %, the melting point of glass becomes excessively high and therefore it becomes difficult to melt the raw materials uniformly.

Accordingly, the lower limit of the $SiO_2$ content is at least 59 mass %, preferably higher than 60 mass %, and more preferably at least 61 mass %. The upper limit of the $SiO_2$ content is 65 mass % or lower, preferably 63 mass % or lower, and more preferably 62 mass % or lower.

The range of the $SiO_2$ content in terms of mass % is $59 \leq SiO_2 \leq 65$, preferably $60 < SiO_2 \leq 65$, more preferably $60 < SiO_2 \leq 63$, further preferably $60 < SiO_2 \leq 62$, and most preferably $61 \leq SiO_2 \leq 62$.

<$Al_2O_3$>

Aluminum oxide ($Al_2O_3$) is a component forming the skeleton of glass. It also adjusts the viscosity and devitrification temperature during glass formation and also improves the water resistance. On the other hand, it also deteriorates the acid resistance of glass. When the $Al_2O_3$ content is lower than 8 mass %, the viscosity and devitrification temperature cannot be adjusted sufficiently or the water resistance cannot be improved sufficiently. On the other hand, when the $Al_2O_3$ content exceeds 15 mass %, the melting point of glass becomes excessively high and therefore it becomes difficult to melt the raw materials uniformly, and the acid resistance also is deteriorated.

Accordingly, the lower limit of the $Al_2O_3$ content is at least 8 mass % and preferably at least 10 mass %. The upper limit of the $Al_2O_3$ content is 15 mass % or lower and preferably lower than 12 mass %.

The range of the $Al_2O_3$ content in terms of mass % is $8 \leq Al_2O_3 \leq 15$, preferably $8 \leq Al_2O_3 \leq 12$, and more preferably $10 \leq Al_2O_3 \leq 12$.

<$SiO_2$—$Al_2O_3$>

The difference ($SiO_2$—$Al_2O_3$) between a component for improving the acid resistance of glass, $SiO_2$, and a component for deteriorating it, $Al_2O_3$, is important for the acid resistance of glass. When the difference ($SiO_2$—$Al_2O_3$) is lower than 47 mass %, the glass cannot have sufficiently high acid resistance. On the other hand, when the difference ($SiO_2$—$Al_2O_3$) exceeds 57 mass %, the devitrification temperature becomes excessively high and thereby it becomes difficult to form glass flakes.

Accordingly, the lower limit of the difference ($SiO_2$—$Al_2O_3$) is at least 47 mass % and preferably higher than 49 mass %. The upper limit of the difference ($SiO_2$—$Al_2O_3$) is 57 mass % or lower, preferably 55 mass % or lower, more preferably 54 mass % or lower, and further preferably 52 mass % or lower.

The range of the difference ($SiO_2$—$Al_2O_3$) in terms of mass % is $47 \leq (SiO_2-Al_2O_3) \leq 57$, preferably $47 \leq (SiO_2-Al_2O_3) \leq 55$, more preferably $49 < (SiO_2-Al_2O_3) \leq 55$, further preferably $49 < (SiO_2-Al_2O_3) \leq 54$, and most preferably $49 < (SiO_2-Al_2O_3) \leq 52$.

<MgO and CaO>

Magnesium oxide (MgO) and calcium oxide (CaO) adjust the viscosity and devitrification temperature during glass formation.

When the MgO content is lower than 1 mass %, the viscosity and devitrification temperature cannot be adjusted sufficiently. On the other hand, when it exceeds 5 mass %, the devitrification temperature becomes excessively high and therefore it becomes difficult to form glass flakes.

Accordingly, the lower limit of the MgO content is at least 1 mass % and preferably at least 3 mass %. The upper limit of the MgO content is 5 mass % or lower and preferably 4 mass % or lower.

The range of the MgO content in terms of mass % is $1 \leq MgO \leq 5$, preferably $3 \leq MgO \leq 5$, and more preferably $3 \leq MgO \leq 4$.

When the CaO content is lower than 20 mass %, the viscosity and devitrification temperature cannot be adjusted sufficiently. On the other hand, when it exceeds 30 mass %, the devitrification temperature becomes excessively high and therefore it becomes difficult to form glass flakes.

Accordingly, the lower limit of the CaO content is at least 20 mass % and preferably at least 21 mass %. The upper limit of the CaO content is 30 mass % or lower, preferably 25 mass % or lower, and more preferably 24 mass % or lower.

The range of the CaO content in terms of mass % is $20 \leq CaO \leq 30$, preferably $20 \leq CaO \leq 25$, and more preferably $21 \leq CaO \leq 24$.

<$Li_2O$, $Na_2O$, and $K_2O$>

Alkali metal oxides ($Li_2O$, $Na_2O$, and $K_2O$) adjust the viscosity and devitrification temperature during glass formation. When no alkali metal oxide is contained, the melting point of glass becomes excessively high and therefore it becomes difficult to melt the raw materials uniformly, and it becomes also difficult to form glass flakes. On the other hand, when the sum of the contents of the alkali metal oxides is 2 mass % or larger, the glass transition temperature is low and the heat resistance of the glass is deteriorated.

Therefore the sum of the contents of $Li_2O$, $Na_2O$, and $K_2O$ is in the range of $0<(Li_2O+Na_2O+K_2O)<2$ in terms of mass %.

Especially, lithium oxide ($Li_2O$) has an effect of lowering the melting point of glass. Accordingly, when it is added, it becomes easy to melt glass raw materials uniformly. Furthermore, since it also has an effect of lowering the working temperature, it becomes easy to form glass flakes.

Accordingly, the range of the $Li_2O$ content in terms of mass % is preferably $0<Li_2O<2$ and more preferably $0<Li_2O \leq 1$. However, $Li_2O$ is not an essential component. Therefore $Li_2O$ need not necessarily be contained, as long as at least one of $Na_2O$ and $K_2O$ is contained.

<$TiO_2$>

Titanium oxide ($TiO_2$) improves the meltability and chemical durability as well as ultraviolet absorption properties of glass. Accordingly, when glass flakes containing $TiO_2$ are mixed, for example, in a resin matrix or coating material, they can suitably prevent the resin matrix or coating material from being deteriorated. However, when the $TiO_2$ content exceeds 5 mass %, the devitrification temperature of glass becomes excessively high and therefore it becomes difficult to form glass flakes.

Accordingly, the lower limit of the $TiO_2$ content is 0 mass % or higher and preferably higher than 0 mass %. The upper limit of the $TiO_2$ content is 5 mass % or lower and preferably 2 mass % or lower.

The range of the $TiO_2$ content in terms of mass % is $0 \leq TiO_2 \leq 5$, preferably $0 \leq TiO_2 \leq 2$, and more preferably $0<TiO_2 \leq 2$.

<Fe>

Usually, iron (Fe) contained in glass is present in the sate of $F^{2+}$ or $Fe^{3+}$. The components $Fe^{3+}$ and $F^{2+}$ improve the ultraviolet absorption properties and heat-ray absorption properties of glass, respectively. Accordingly, although iron (Fe) is not essential, it can be used as a component for adjusting the optical properties of glass. Moreover, iron (Fe) may be contained inevitably due to industrial raw materials even when it is not intended to be contained.

Accordingly, the upper limit of the iron (Fe) content in terms of $Fe_2O_3$ is 5 mass % or lower, preferably 2 mass % or lower, more preferably 0.5 mass % or lower, and further preferably 0.1 mass % or lower.

The range of the $Fe_2O_3$ content in terms of mass % is $0 \leq Fe_2O_3 \leq 5$, preferably $0 \leq Fe_2O_3 \leq 2$, further preferably $0 \leq Fe_2O_3 \leq 0.5$, and most preferably $0 \leq Fe_2O_3 \leq 0.1$.

<$SO_3$>

Sulfur trioxide ($SO_3$) is not an essential component but can be used as a fining agent. When the raw materials of sulfate are used as glass raw materials, 0.5 mass % or less of sulfur trioxide may be contained in some cases.

<$B_2O_3$>

Substantially no diboron trioxide ($B_2O_3$) is allowed to be contained in the present invention.

<F>

Substantially no fluorine (F) is allowed to be contained in the present invention.

<ZnO>

Substantially no zinc oxide (ZnO) is allowed to be contained in the present invention.

<BaO and SrO>

Substantially no strontium oxide (SrO) and barium oxide (BaO) are allowed to be contained in the present invention.

<$ZrO_2$>

Substantially no zirconium oxide ($ZrO_2$) is allowed to be contained in the present invention.

In the present invention, the expression "substantially no substance is allowed to be contained" denotes that it is not intended to be contained except for the case where it is contained inevitably, for instance, due to an industrial raw material. Specifically, it denotes a content lower than 0.1 mass %, preferably lower than 0.05 mass %, and more preferably lower than 0.03 mass %.

As described above, the glass composition of the glass flakes according to the present invention includes, as essential components, $SiO_2$, $Al_2O_3$, MgO, CaO and ($Li_2O+Na_2O+K_2O$), and preferably contains $TiO_2$. Furthermore, it can be composed of only these components. If necessary, it can contain iron oxide (FeO and/or $Fe_2O_3$) or $SO_3$.

[Physical Properties of Glass Flakes]

The respective physical properties of the glass flakes according to the present invention are described below in detail.

<Temperature Property>

The temperature at which the viscosity of molten glass is 1000 dPa·sec (1000 poise) is called "working temperature" and is considered to be the most suitable temperature for forming glass flakes.

The glass flakes can be produced, for example, using a production apparatus as shown in FIG. 1. A glass base material 11 molten in a refractory furnace vessel 12 is blown up into a balloon shape with gas fed into a blow nozzle 15 to be formed into a hollow glass film 16. The hollow glass film 16 is crushed with pressure rolls 17 and thus glass flakes 1 are obtained. The hollow glass film 16 has an average thickness of 0.1 μm to 15 μm. When such a thin hollow glass film 16 is to be formed, the glass temperature decreases considerably. Accordingly, the plasticity of the hollow glass film 16 is deteriorated rapidly and it becomes difficult to be stretched. Furthermore, the deterioration in plasticity makes it difficult for the hollow glass film 16 to grow uniformly and thereby variations in glass film thickness may occur. Therefore the working temperature is preferably at least 1200° C. and more preferably at least 1220° C.

However, when the working temperature exceeds 1300° C., the apparatus for producing glass tends to be eroded by heat and thus the apparatus life becomes shorter. With the decrease in working temperature, the fuel cost required for melting glass raw materials can be reduced. Accordingly, the working temperature is preferably 1265° C. or lower, more preferably 1255° C. or lower, and further preferably 1250° C. or lower.

Furthermore, with an increase in temperature difference ΔT obtained by subtracting the devitrification temperature from the working temperature, devitrification tends not to occur during glass formation and thus further homogeneous glass flakes can be produced with a high yield. In the case of glass with a temperature difference ΔT of at least 30° C., glass flakes can be produced with a high yield, for example, using the production apparatus as shown in FIG. 1. Accordingly, the temperature difference ΔT is preferably at least 30° C., more preferably at least 35° C., and further preferably at least 40° C. However, the temperature difference ΔT is preferably at most 70° C. because in that case, the glass composition can be adjusted easily. Further preferably, the temperature difference ΔT is at most 60° C.

The term "devitrification" denotes that crystals that have been formed and have grown in a molten glass base material cause it to be cloudy. Glass produced from such a molten glass base material may contain crystallized mass and therefore is not preferred as glass flakes.

<Glass Transition Point>

A higher glass transition point of glass flakes allows them to have higher heat resistance and to tend not to be deformed through processing that involves heating at a high temperature. When the glass transition point is at least 600° C., there is little possibility that the glass flakes will be deformed in the step of forming a coating film composed mainly of metal and/or metal oxide on the surface of each glass flake. Furthermore, glass flakes or glass flakes with a coating film can be mixed in a coating material, which can be used suitably for a baking finish, for example. The glass composition ranges defined in the present invention make it possible to obtain glass with a glass transition point of at least 600° C. easily. The glass transition point of the glass flakes according to the present invention is preferably at least 600° C., more preferably at least 650° C., and further preferably at least 700° C.

<Chemical Durability>

The glass flakes of the present invention are excellent in chemical durability such as acid resistance, water resistance, and alkali resistance. Accordingly, the glass flakes of the present invention can be mixed suitably, for example, in resin moldings, coating materials, cosmetics, and inks.

The index of acid resistance to be used herein is a mass reduction rate $\Delta W_1$ obtained when granular glass with an average grain size of 420 μm to 590 μm was immersed in a 10-mass % sulfuric acid aqueous solution with a temperature of 80° C. for 72 hours. Lower mass reduction rates $\Delta W_1$ indicate higher acid resistance. The method of measurement thereof is in accordance with "Measuring Method for Chemical Durability of Optical Glass (Powder Method) 06-1975" of Japan Optical Glass Industrial Standards (JOGIS). However, a 0.01N nitric acid aqueous solution is used in the measurement method of JOGIS, but a 10-mass % sulfuric acid aqueous solution is used in the examples described later in this specification. Furthermore, the temperature of the sulfuric acid aqueous solution is set at 80° C., and the process time in the examples is 72 hours instead of 60 minutes employed in the measurement method of JOGIS.

When, for example, a coating material containing glass flakes is used as a corrosion-resistant liner in an acid environment, it is desirable that the glass have an acid resistance of 1.50 mass % or lower in terms of the above-mentioned index (mass reduction rate $\Delta W_1$). When the mass reduction rate $\Delta W_1$ is higher than that, it cannot be expected to obtain the corrosion resistance to be provided by the corrosion-resistant liner in the acid environment. The acid resistance of the glass in terms of the above-mentioned index is more preferably 0.80 mass % or lower and further preferably 0.50 mass % or lower.

The alkali resistance can be measured by using a sodium hydroxide aqueous solution instead of the sulfuric acid aqueous solution employed for the method of measuring the acid resistance. The index of the alkali resistance to be used herein is a mass reduction rate $\Delta W_2$. The lower the mass reduction rate $\Delta W_2$, the higher the alkali resistance.

When glass flakes are used in a strong alkaline environment, for instance, in a battery separator, it is desirable that the alkali resistance of the glass in terms of the above-mentioned index (mass reduction rate $\Delta W_2$) be 3 mass % or lower. When the mass reduction rate $\Delta W_2$ is higher than that, the components of the glass flakes elute into an electrolyte and the function of the separator may be damaged. The alkali resistance of the glass in terms of the above-mentioned index is preferably 2.0 mass % or lower, more preferably 1.5 mass % or lower, and further preferably 1.0 mass % or lower.

[Glass Flakes with Coating Film]

Figure 3:
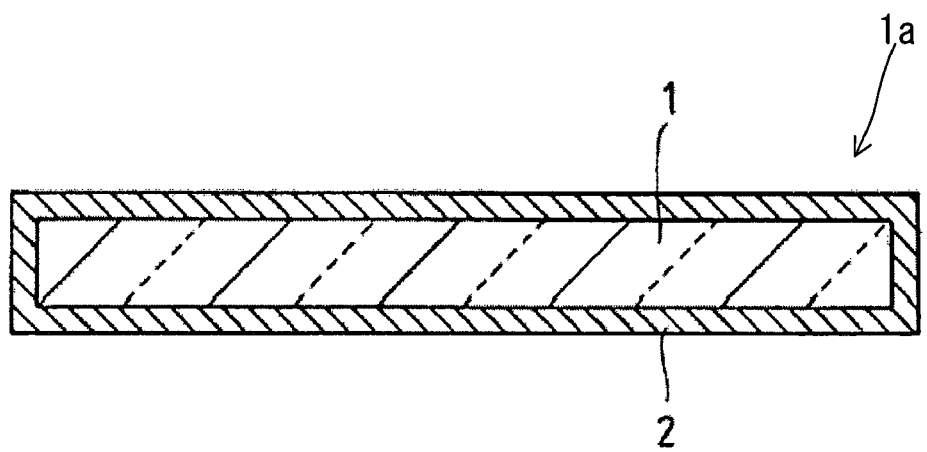
FIG. 3 is a schematic sectional view showing a glass flake with a coating layer.

With the aforementioned glass flake 1 used as a substrate, a coating film 2 composed mainly of metal and/or metal oxide is formed on the surface thereof. Thus a glass flake with a coating film 1a can be produced (see FIG. 3). Preferably, the coating film 2 is formed substantially of metal and/or metal oxide.

The coating film 2 can be formed using at least one metal selected from the group consisting of silver, gold, platinum, palladium, and nickel. It can be in the form of a monolayer, a mixed layer, or multiple layers.

Furthermore, the coating film 2 can be formed using at least one metal oxide selected from the group consisting of titanium oxide, aluminum oxide, iron oxide, cobalt oxide, zirconium oxide, zinc oxide, tin oxide, and silicon oxide. It can be in the form of a monolayer, a mixed layer, or multiple layers. Especially, titanium dioxide and iron oxide are preferred. The titanium dioxide has a high refractive index and transparency and develops excellent interference colors. The iron oxide can develop characteristic interference colors.

Furthermore, the coating film 2 can be a layered film formed by stacking a first film composed mainly of metal and a second film composed mainly of metal oxide. It is not necessary to form the coating film 2 on the whole surface of the glass flake 1 that serves as a substrate. The coating film 2 can be formed on part of the surface of the glass flake 1.

The thickness of the coating film 2 can be selected suitably according to the intended use. The method of forming the coating film 2 on the surface of the glass flake 1 can be any one of generally known methods. Examples of the method that can be used include known methods such as a sputtering method, a sol-gel method, a CVD method, an LPD method, and a liquid phase method in which oxides are allowed to deposit from metal salts onto the surface thereof.

[Mixing of Glass Flakes in, for Example, Resin Compositions, Coating Materials, Ink Compositions, and Cosmetics]

The glass flake 1 or glass flake with a coating film 1a is mixed as a pigment or reinforcing filler, for example, in resin compositions, coating materials, ink compositions, or cosmetics by a known method. This improves the color tone and luster thereof as well as, for instance, dimensional accuracy and strength in the resin compositions, coating materials, and ink compositions.

Figure 4:
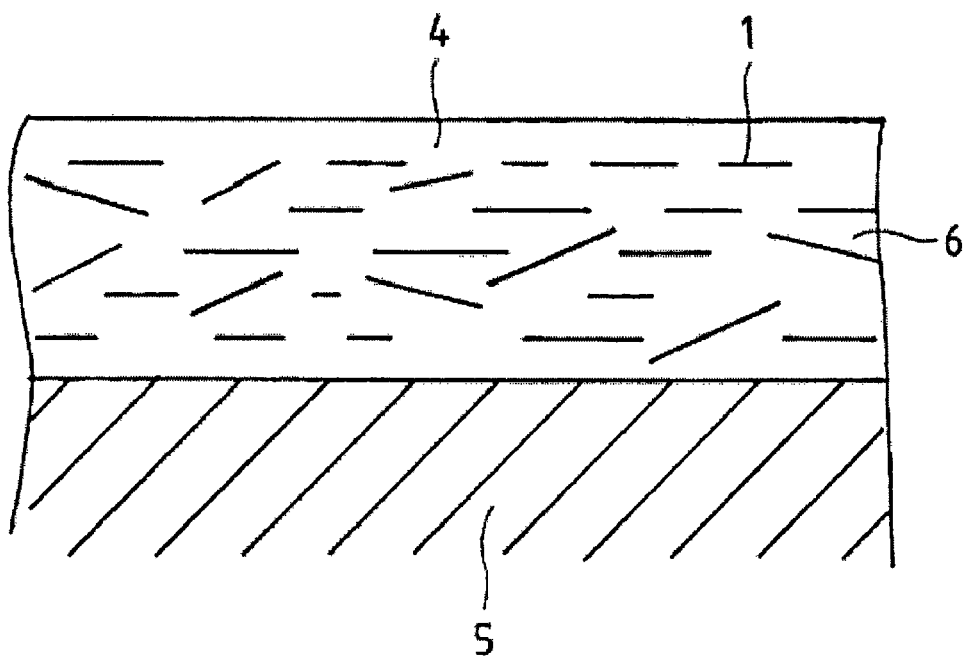
FIG. 4 is a schematic sectional view showing a resin composition containing glass flakes of the present invention.

FIG. 4 is a schematic sectional view for explaining an example in which glass flakes 1 were mixed in a coating material, which was then applied to the surface of a substrate 5. The glass flakes 1 are dispersed in a resin matrix 4 of a coating film 6.

The resin composition, coating material, ink composition, or cosmetic to be used can be selected suitably according to the intended use as long as it is generally known. Furthermore, the mixing ratio between the glass flakes and the material to be mixed also can be selected suitably. Moreover, the method of mixing the glass flakes and the material together can be any method as long as it is generally known.

For instance, when the glass flakes are mixed in a coating material, a thermosetting resin, thermoplastic resin, or curing agent can be selected suitably to be used for a matrix resin.

Examples of the thermosetting resin include acrylic resin, polyester resin, epoxy resin, phenolic resin, urea resin, fluororesin, polyester-urethane curable resin, epoxy-polyester curable resin, acrylic-polyester resin, acrylic-urethane curable resin, acrylic-melamine curable resin, and polyester-melamine curable resin.

Examples of the thermoplastic resin include polyethylene resin, polypropylene resin, petroleum resin, thermoplastic polyester resin, and thermoplastic fluororesin.

Furthermore, examples of the curing agent include polyisocyanate, amine, polyamide, polybasic acid, acid anhydride, polysulfide, trifluoroborate, acid dihydrazide, and imidazole.

When the glass flakes are mixed in a resin composition, the aforementioned various thermosetting or thermoplastic resins can be used for the matrix resin.

Examples of the ink composition include inks for writing instruments, such as various kinds of ball-point pens and felt-tip pens, and printing inks, such as gravure ink and offset ink. Any one of them can be used as the ink composition.

The vehicle of the ink composition has a function of dispersing a pigment and fixing ink to paper. The vehicle is composed of, for example, resins, oil, and a solvent.

Vehicles of inks for writing instruments contain, as a resin, acrylic resin, styrene-acrylic copolymer, polyvinyl alcohol, polyacrylate, acrylic-vinyl acetate copolymer, microbially produced polysaccharide such as xanthan gum, or water-soluble plant polysaccharide such as guar gum. Furthermore, the vehicles contain, for example, water, alcohol, hydrocarbon, or ester as a solvent.

Vehicles for gravure inks contain, as a resin, gum rosin, wood rosin, toll oil rosin, lime rosin, rosin ester, maleic resin, polyamide resin, vinyl resin, cellulose nitrate, cellulose acetate, ethyl cellulose, chlorinated rubber, cyclized rubber, ethylene-vinyl acetate copolymer resin, urethane resin, polyester resin, alkyd resin, a resin mixture of, for example, gilsonite, dammar, or shellac, mixtures of the resins described above, aqueous emulsion resins or water-soluble resins obtained by water-solubilizing the resins described above. Furthermore, the vehicles contain, for example, hydrocarbon, alcohol, ether, ester, or water as a solvent.

Vehicles for offset inks contain: as a resin, rosin-modified phenolic resin, petroleum resin, alkyd resin, or a dry-modified resin thereof, and as oil, a plant oil such as linseed oil, tung oil, or soybean oil. Furthermore, the vehicles contain, for example, n-paraffin, isoparaffin, aromatic, naphthene, alpha-olefin, or water as a solvent.

Moreover, suitably selected common additives, such as dyes, pigments, various types of surfactants, lubricants, anti-foaming agents, and leveling agents, can be mixed in the above-mentioned various vehicle components.

Examples of cosmetics include a wide range of cosmetics such as facial cosmetics, makeup cosmetics, and hair cosmetics. Among them, especially in makeup cosmetics such as foundation, face powder, eye shadow, blusher, makeup base, nail enamel, eyeliner, mascara, lipstick, and fancy powder, the glass flakes are used suitably.

The glass flakes can be subjected to a hydrophobizing treatment suitably accordingly to the purpose of the cosmetics. Examples of the method of carrying out the hydrophobizing treatment include the following five methods:

(1) a treatment method to be carried out using methyl hydrogen polysiloxane, high viscosity silicone oil, or a silicone compound such as a silicone resin;
(2) a treatment method to be carried out using a surfactant such as an anion activator or a cation activator;
(3) a treatment method to be carried out using a polymer compound such as nylon, polymethyl methacrylate, polyethylene, various types of fluororesins (such as polytetrafluoroethylene resin (PTFE), a tetrafluoroethylene-perfluoroalkyl vinyl ether copolymer (PFA), a tetrafluoroethylene-hexafluoropropylene copolymer (FEP), a tetrafluoroethylene-ethylene copolymer (ETFE), polyvinylidene fluoride (PVDF), and polychloro-trifluoroethylene (PCTFE)), or polyamino acid;
(4) a treatment method to be carried out using, for example, a perfluoro group-containing compound, lecithin, collagen, metallic soap, lipophilic wax, or polyhydric alcohol partial ester or whole ester; and
(5) a treatment method employing a combination thereof.

However, any method other than the above-mentioned methods also can be used as long as it can be used generally for the hydrophobizing treatment of powder.

Moreover, other materials that are used usually for cosmetics can be mixed suitably in the cosmetics as required. Examples thereof include inorganic powder, organic powder, pigments, dyes, hydrocarbon, esters, oil components, organic solvents, resins, plasticizers, ultraviolet absorbers, antioxidants, preservatives, surfactants, moisturizing agents, fragrances, water, alcohol, and thickeners.

Examples of the inorganic powder include talc, kaolin, sericite, muscovite, phlogopite, lepidolite, biotite, lithia mica, vermiculite, magnesium carbonate, calcium carbonate, diatomaceous earth, magnesium silicate, calcium silicate, aluminum silicate, barium sulphate, metal tungstate, silica, hydroxyapatite, zeolite, boron nitride, and ceramic powder.

Examples of the organic powder include nylon powder, polyethylene powder, polystyrene powder, benzoguanamine powder, polytetrafluoroethylene powder, distyrenebenzene polymer powder, epoxy powder, acrylic powder, and microcrystalline cellulose.

Pigments are classified broadly into inorganic pigments and organic pigments.

Examples of inorganic pigments, which are described by being broken down by color, include:
  inorganic white pigments: titanium oxide, zinc oxide, etc.;
  inorganic red pigments: iron oxide (red iron oxide), iron titanate, etc.;
  inorganic brown pigments: gamma iron oxide, etc.;
  inorganic yellow pigments: yellow iron oxide, yellow ocher, etc.;
  inorganic black pigments: black iron oxide, carbon black, etc.;
  inorganic violet pigments: mango violet, cobalt violet, etc.;
  inorganic green pigments: cobalt titanate, etc.; and
  inorganic blue pigments: ultramarine, indigo, etc.

Examples of pearl pigments include titanium oxide coated mica, titanium oxide coated bismuth oxychloride, bismuth oxychloride, titanium oxide coated talc, argentine, and colored titanium oxide coated mica. Furthermore, examples of metal powder pigments include aluminum powder and copper powder.

Examples of organic pigments include:
  red color No. 201, red color No. 202, red color No. 204, red color No. 205, red color No. 220, red color No. 226, red color No. 228, red color No. 405, orange color No. 203, orange color No. 204, yellow color No. 205, yellow color No. 401, and blue color No. 404; and organic pigments obtained by forming lakes of the following dyes with fillers such as talc, calcium carbonate, barium sulfate, zirconium oxide, or aluminum white:

red color No. 3, red color No. 104, red color No. 106, red color No. 227, red color No. 230, red color No. 401, red color No. 505, orange color No. 205, yellow color No. 4, yellow color No. 5, yellow color No. 202, yellow color No. 203, green color No. 3, and blue color No. 1.

Furthermore, examples of dyes include natural dyes such as chlorophyll and beta-carotene.

Examples of hydrocarbon include:

squalane, liquid paraffin, vaseline, microcrystalline wax, ozokerite, ceresin, myristic acid, palmitic acid, stearic acid, oleic acid, isostearic acid, cetyl alcohol, hexadecyl alcohol, oleyl alcohol, cetyl-2-ethyl hexanoate, 2-ethylhexyl palmitate, 2-octyldodecyl myristate, di-2-neopentylglycol ethyl hexanoate, tri-2-glyceryl ethyl hexanoate, 2-octyldodecyl oleate, isopropyl myristate, glycerol triisostearate, glycerol tri-coconut oil fatty acid, olive oil, avocado oil, beeswax, myristyl myristate, mink oil, and lanoline;

further silicone oil, higher fatty acid, esters of oils and fats, higher alcohol, and oil components such as wax; organic solvents such as acetone, toluene, butyl acetate, and ester acetate; resins such as alkyd resin and urea resin; plasticizers such as camphor and acetyl tributyl citrate; and ultraviolet absorbers, antioxidants, preservatives, surfactants, moisturizing agents, fragrances, water, alcohol, and thickeners.

The form of the cosmetics is not particularly limited. Examples thereof include powder, cake, pencil, stick, ointment, liquid, emulsion, and cream.

EXAMPLES

Hereinafter, the present invention is described further in detail using examples and comparative examples.

Examples 1 to 15 and Comparative Examples 1 to 3

Common glass raw materials such as silica were mixed together so that the compositions indicated in Tables 1 to 3 were obtained, and thereby batches of the respective examples and comparative examples were prepared. These batches were heated to 1400° C. to 1600° C. with an electric furnace to be melted. They were kept in this state for about four hours to have uniform compositions. Thereafter, each molten glass was poured onto an iron plate and was cooled slowly to normal temperature. Thus glass samples were obtained.

Glasses thus produced were measured for thermal expansion curves using a commercial dilatometer and then glass transition points thereof were determined from the thermal expansion curves. Moreover, the relationship between viscosity and temperature was examined by a common platinum ball pulling method and then the working temperature was determined from the results. Further, crushed glass with a grain size of 1.0 mm to 2.8 mm was placed in a platinum boat and then was heated for two hours in an electric furnace with a temperature gradient (900° C. to 1400° C.). Then the devitrification temperature was determined from the maximum temperature of the place in the electric furnace corresponding to the position where a crystal appeared. The temperature in the electric furnace has been measured beforehand and the glass placed in a predetermined position is heated at that temperature.

These measurement results are indicated in Tables 1 to 3. With respect to the glass compositions indicated in the tables, all the values are indicated in mass %. As described above, $\Delta T$ denotes the difference in temperature obtained by subtracting the devitrification temperature from the working temperature. As described above, $\Delta W_1$ denotes the index of acid resistance and is expressed by the mass reduction rate obtained when granular glass with an average grain size of 420 μm to 590 μm was immersed in a 10-mass % sulfuric acid aqueous solution with a temperature of 80° C. for 72 hours. As described above, $\Delta W_2$ denotes the index of the alkali resistance and is expressed by the mass reduction rate obtained when granular glass with an average grain size of 420 μm to 590 μm was immersed in a 10-mass % sodium hydroxide aqueous solution with a temperature of 80° C. for 72 hours.

TABLE 1

| mass % | Example 1 | Example 2 | Example 3 | Example 4 | Example 5 | Example 6 | Example 7 | Example 8 | Example 9 |
|---|---|---|---|---|---|---|---|---|---|
| $SiO_2$ | 61.45 | 61.47 | 61.45 | 61.06 | 61.98 | 61.67 | 61.89 | 61.55 | 61.55 |
| $Al_2O_3$ | 11.18 | 11.18 | 11.18 | 11.20 | 11.19 | 10.38 | 11.17 | 11.20 | 11.20 |
| $SiO_2 - Al_2O_3$ | 50.27 | 50.29 | 50.27 | 49.86 | 50.79 | 51.29 | 50.72 | 50.35 | 50.35 |
| MgO | 3.17 | 3.19 | 3.03 | 3.14 | 3.04 | 3.27 | 3.15 | 3.21 | 3.21 |
| CaO | 22.80 | 22.96 | 21.77 | 22.53 | 21.79 | 23.48 | 22.62 | 23.05 | 23.05 |
| $Li_2O$ | 0.14 | 0.14 | 0.36 | 0.28 | 0.27 | — | — | 0.19 | 0.09 |
| $Na_2O$ | 0.30 | 0.10 | 0.38 | 0.58 | 0.56 | 0.40 | 0.39 | — | 0.39 |
| $K_2O$ | 0.45 | 0.45 | 0.28 | 0.29 | 0.29 | 0.29 | 0.29 | 0.29 | — |
| $Li_2O + Na_2O + K_2O$ | 0.89 | 0.69 | 1.02 | 1.15 | 1.12 | 0.69 | 0.68 | 0.48 | 0.48 |
| $TiO_2$ | 0.25 | 0.25 | 1.56 | 0.92 | 0.89 | 0.25 | 0.25 | 0.25 | 0.25 |
| $Fe_2O_3$ | 0.26 | 0.26 | — | — | — | 0.26 | 0.24 | 0.26 | 0.26 |
| Glass transition point [° C.] | 729 | 739 | 711 | 715 | 717 | 744 | 748 | 735 | 741 |
| Devitrification Temp. [° C.] | 1207 | 1211 | 1199 | 1195 | 1205 | 1228 | 1218 | 1211 | 1220 |
| Working Temp. [° C.] | 1250 | 1248 | 1242 | 1232 | 1253 | 1248 | 1263 | 1243 | 1252 |
| $\Delta T$ [° C.] | 43 | 37 | 43 | 37 | 48 | 20 | 45 | 32 | 32 |
| $\Delta W_1$ [mass %] | 0.41 | 0.37 | 0.30 | 0.32 | 0.25 | 0.25 | 0.26 | 0.21 | 0.25 |
| $\Delta W_2$ [mass %] | 1.68 | 1.67 | 1.60 | 1.52 | 1.47 | 1.81 | 1.71 | 1.60 | 1.57 |

TABLE 2

| mass % | Example 10 | Example 11 | Example 12 | Example 13 | Example 14 | Example 15 |
|---|---|---|---|---|---|---|
| $SiO_2$ | 61.47 | 61.16 | 60.90 | 60.84 | 60.37 | 59.79 |
| $Al_2O_3$ | 11.18 | 11.13 | 11.08 | 11.16 | 12.72 | 12.34 |
| $SiO_2 - Al_2O_3$ | 50.29 | 50.03 | 49.82 | 49.68 | 47.65 | 47.45 |
| MgO | 3.21 | 3.09 | 3.12 | 3.20 | 3.07 | 3.18 |

TABLE 2-continued

| mass % | Example 10 | Example 11 | Example 12 | Example 13 | Example 14 | Example 15 |
|---|---|---|---|---|---|---|
| CaO | 23.20 | 22.17 | 22.44 | 22.97 | 22.07 | 22.85 |
| $Li_2O$ | — | — | — | — | — | — |
| $Na_2O$ | 0.39 | 0.37 | 0.37 | 0.38 | 0.37 | 0.38 |
| $K_2O$ | 0.29 | 0.28 | 0.29 | 0.29 | 0.27 | 0.29 |
| $Li_2O + Na_2O + K_2O$ | 0.68 | 0.65 | 0.66 | 0.67 | 0.64 | 0.67 |
| $TiO_2$ | — | 1.55 | 0.25 | 0.90 | 0.87 | 0.90 |
| $Fe_2O_3$ | 0.26 | 0.26 | 1.55 | 0.26 | 0.26 | 0.26 |
| Glass transition point [° C.] | 749 | 749 | 746 | 743 | 754 | 747 |
| Devitrification Temp. [° C.] | 1216 | 1202 | 1213 | 1204 | 1195 | 1203 |
| Working Temp. [° C.] | 1253 | 1253 | 1250 | 1250 | 1265 | 1249 |
| ΔT [° C.] | 37 | 51 | 37 | 46 | 70 | 46 |
| $\Delta W_1$ [mass %] | 0.25 | 0.30 | 0.28 | 0.35 | 0.34 | 0.49 |
| $\Delta W_2$ [mass %] | 1.75 | 1.55 | 1.74 | 1.63 | 1.55 | 1.57 |

TABLE 3

| mass % | Comparative Example 1 | Comparative Example 2 | Comparative Example 3 |
|---|---|---|---|
| $SiO_2$ | 72.76 | 59.10 | 58.08 |
| $Al_2O_3$ | 1.88 | 13.10 | 14.29 |
| $SiO_2 - Al_2O_3$ | 70.88 | 46.00 | 43.79 |
| MgO | 3.58 | 2.83 | 3.16 |
| CaO | 7.62 | 24.31 | 22.66 |
| $Li_2O$ | — | — | — |
| $Na_2O$ | 13.20 | 0.03 | 0.38 |
| $K_2O$ | 0.95 | 0.23 | 0.29 |
| $Li_2O + Na_2O + K_2O$ | 14.15 | 0.26 | 0.67 |
| $TiO_2$ | — | 0.04 | 0.89 |
| $Fe_2O_3$ | — | 0.36 | 0.26 |
| Glass transition point [° C.] | 553 | 758 | 751 |
| Devitrification Temp. [° C.] | 1020 | 1202 | 1198 |
| Working Temp. [° C.] | 1172 | 1246 | 1247 |
| ΔT [° C.] | 152 | 44 | 49 |
| $\Delta W_1$ [mass %] | 0.40 | 0.90 | 1.64 |
| $\Delta W_2$ [mass %] | 14.20 | 1.27 | 1.52 |

The glass transition points of the glasses according to Examples 1 to 15 were 711° C. to 754° C. This indicates that these glasses have excellent heat resistance.

The working temperatures of these glasses were 1232° C. to 1265° C. These temperatures are suitable for producing glass flakes.

The differences ΔT (working temperature–devitrification temperature) of these glasses were 20° C. to 70° C. These differences do not cause devitrification in the process of producing glass flakes.

Furthermore, these glasses had mass reduction rates $\Delta W_1$, the index of acid resistance, of 0.21 mass % to 0.49 mass %. This indicates that these glass flakes have excellent acid resistance.

Moreover, these glasses had mass reduction rates $\Delta W_2$, the index of alkali resistance, of 1.47 mass % to 1.81 mass %. This indicates that these glass flakes have excellent alkali resistance.

The glass of Comparative Example 1 was made of a sheet glass composition (soda-lime composition) that had been provided conventionally. However, this glass had a glass transition point of lower than 600° C. Thus it was proved that the heat resistance thereof was not sufficiently high.

Furthermore, the glass of Comparative Example 1 had a mass reduction rate $\Delta W_2$ of 14.20 mass %, which was 7.85 to 9.66 times the mass reduction rates $\Delta W_2$, 1.47 mass % to 1.81 mass %, of the glasses according to Examples 1 to 15.

With respect to the glass of Comparative Example 2, the contents of silicon dioxide ($SiO_2$) and aluminum oxide ($Al_2O_3$) are within the glass composition range of the present invention when considered individually. However, the difference therebetween ($SiO_2$—$Al_2O_3$) was lower by about 1 mass % to 3 mass % as compared to the glass composition range defined in the present invention and by about 1.45 mass % to 5.29 mass % as compared to the compositions of the glasses according to Examples 1 to 15.

The mass reduction rate $\Delta W_1$ of the glass according to Comparative Example 2 was 0.90 mass %, which was 1.84 to 4.29 times the mass reduction rates $\Delta W_1$, 0.21 mass % to 0.49 mass %, of the glasses according to Examples 1 to 15.

With respect to the glass of Comparative Example 3, the content of aluminum oxide ($Al_2O_3$) is within the glass composition range of the present invention, but the content of silicon dioxide ($SiO_2$) is out of the glass composition range. Moreover, the difference therebetween ($SiO_2$—$Al_2O_3$) was lower by about 3 mass % to 5 mass % as compared to the glass composition range defined in the present invention and by about 3.66 mass % to 7.50 mass % as compared to the compositions of the glasses according to Examples 1 to 15.

The mass reduction rate $\Delta W_1$ of the glass according to Comparative Example 3 was 1.64 mass %, which was 3.35 to 7.81 times the mass reduction rates $\Delta W_1$, 0.21 mass % to 0.49 mass %, of the glasses according to Examples 1 to 15.

Thus it was found that the acid resistance varied according to the value of ($SiO_2$—$Al_2O_3$) in the composition of the glass according to the present invention. Furthermore, it was proved that the glasses in which the contents of $SiO_2$ and $Al_2O_3$ as well as the value of ($SiO_2$—$Al_2O_3$) are within the composition range of the present invention had excellent acid resistance. Therefore it was proved that the value of ($SiO_2$—$Al_2O_3$) was effective as an index of the acid resistance of a glass composition.

Glasses having the compositions of the present invention were found to have excellent alkali resistance.

Subsequently, with glasses of Examples 1 to 15, glass flakes and glass flakes with a coating film were produced. First, glass having each composition was re-melted in an electric furnace. This was formed into pellets while being cooled. These pellets were placed in a production apparatus as shown in FIG. 1 and thus glass flakes with an average thickness of 1 μm were produced.

Application Examples 1 and 2

Glass flakes having the compositions of Examples 1 and 3 thus produced each were crushed to have suitable grain sizes. Thereafter, the surfaces of the glass flakes were coated with titanium dioxide by a liquid phase method. This liquid phase method was one described in JP 2003-012962 A, i.e. a method of allowing titanium dioxide to deposit on the surfaces of glass flakes from metal salt. The glass flakes with a coating film thus produced were observed with an electron microscope and thereby it was confirmed that a titanium dioxide coating film had been formed on the surface of each glass flake.

Application Examples 3 and 4

Glass flakes having the compositions of Examples 1 and 3 each were crushed to have suitable grain sizes. Thereafter, the surfaces of the glass flakes were coated with silver by common electroless plating. This common electroless plating was one described in Comparative Example 2 of JP 2003-012962 A. The glass flakes with a coating film thus produced were observed with an electron microscope and thereby it was confirmed that a silver coating film had been formed on the surface of each glass flake.

Application Examples 5 and 6

Glass flakes having the compositions of Examples 1 and 3 each were crushed to have suitable grain sizes. Thereafter, this was mixed with polyester resin and thereby a polyester resin composition containing glass flakes was obtained.

Application Examples 7 and 8

The glass flakes with a coating film of Application Examples 1 and 2 each were mixed with epoxy acrylate and thereby a vinyl ester coating material containing glass flakes with a coating film was obtained.

Application Examples 9 and 10

The glass flakes with a coating film of Application Examples 1 and 2 each were mixed with foundation, a facial cosmetic, and thereby a cosmetic containing glass flakes with a coating film was obtained.

Application Examples 11 and 12

The glass flakes with a coating film of Application Examples 1 and 2 each were mixed with an ink composition obtained by suitably mixing a colorant, resin, and an organic solvent. Thus an ink composition containing glass flakes with a coating film was obtained.

The invention claimed is:

1. A glass flake, having a composition comprising, in terms of mass %:
   $61 < SiO_2 \leq 65$,
   $8 \leq Al_2O_3 < 12$,
   $49 < (SiO_2 - Al_2O_3) \leq 57$,
   $3 \leq MgO \leq 3.5$,
   $20 \leq CaO \leq 22.62$,
   $0 < (Li_2O + Na_2O + K_2O) < 2$,
   $0 \leq TiO_2 \leq 5$, and
   $Li_2 < 0.36$,
   wherein a content ratio of $SiO_2$ to $(MgO + CaO)$ is no less than 2.37 and no greater than 2.83,
   wherein a content of each of $B_2O_3$, F, ZnO, BaO, SrO, and $ZrO_2$ in the composition is less than 0.1 mass %, and
   wherein the glass flake has an index of acid resistance in terms of a mass reduction rate $\Delta W_1$ of 0.80 mass % or lower.

2. The glass flake according to claim 1, wherein the range of $(SiO_2 - Al_2O_3)$ is $49 < (SiO_2 - Al_2O_3) < 55$.

3. The glass flake according to claim 1, wherein when a temperature at which glass has a viscosity of 1000 dPa·sec is defined as a working temperature, the working temperature is 1265° C. or lower.

4. The glass flake according to claim 3, wherein a temperature difference $\Delta T$ obtained by subtracting devitrification temperature from the working temperature is at least 30° C.

5. A surface-coated glass flake, comprising:
   a glass flake according to claim 1; and
   a coating film that is composed mainly of metal and/or metal oxide and that covers a surface of the glass flake.

6. The surface-coated glass flake according to claim 5, wherein the metal is at least one selected from the group consisting of nickel, gold, silver, platinum, and palladium.

7. The surface-coated glass flake according to claim 5, wherein the metal oxide is at least one selected from the group consisting of titanium oxide, aluminum oxide, iron oxide, cobalt oxide, zirconium oxide, zinc oxide, tin oxide, and silicon oxide.

8. A resin composition comprising a glass flake having a composition comprising, in terms of mass%:
   $61 < SiO_2 \leq 65$,
   $8 \leq Al_2O_3 < 12$,
   $49 < (SiO_2 - Al_2O_3) \leq 57$,
   $3 \leq MgO \leq 3.5$,
   $20 \leq CaO \leq 22.62$,
   $0 < (Li_2O + Na_2O + K_2O) < 2$,
   $0 \leq TiO_2 \leq 5$, and
   $Li_2 < 0.36$,
   wherein a content ratio of $SiO_2$ to $(MgO + CaO)$ is no less than 2.37,
   wherein a content of each of $B_2O_3$, F, ZnO, BaO, SrO, and $ZrO_2$ in the composition is less than 0.1 mass %, and
   wherein the glass flake has an index of acid resistance in terms of a mass reduction rate $\Delta W_1$ of 0.80 mass % or lower, or a resin composition comprising the surface-coated glass flake according to claim 5.

9. A coating material comprising a glass flake having a composition comprising, in terms of mass%:
   $61 < SiO_2 \leq 65$,
   $8 \leq Al_2O_3 < 12$,
   $49 < (SiO_2 - Al_2O_3) \leq 57$,
   $3 \leq MgO \leq 3.5$,
   $20 \leq CaO \leq 22.62$,
   $0 < (Li_2O + Na_2O + K_2O) < 2$,
   $0 \leq TiO_2 \leq 5$, and
   $Li_2 < 0.36$,
   wherein a content ratio of $SiO_2$ to $(MgO + CaO)$ is no less than 2.37,
   wherein a content of each of $B_2O_3$, F, ZnO, BaO, SrO, and $ZrO_2$ in the composition is less than 0.1 mass %, and
   wherein the glass flake has an index of acid resistance in terms of a mass reduction rate $\Delta W_1$ of 0.80 mass % or lower,
   or a coating material comprising the surface-coated glass flake according to claim 5.

10. An ink composition comprising a glass flake having a composition comprising, in terms of mass%:
    $61 < SiO_2 \leq 65$,
    $8 \leq Al_2O_3 < 12$,
    $49 < (SiO_2 - Al_2O_3) \leq 57$,
    $3 \leq MgO \leq 3.5$,
    $20 \leq CaO \leq 22.62$,
    $0 < (Li_2O + Na_2O + K_2O) < 2$,
    $0 \leq TiO_2 \leq 5$, and
    $Li_2 < 0.36$, wherein a content ratio of SiO, to (MgO+CaO) is no less than 2.37, wherein a content of each of $B_2O_3$, F, ZnO, BaO, SrO, and $ZrO_2$ in the composition is less than 0.1 mass %, and wherein the glass flake has an index of acid resistance in terms of a mass reduction rate $\Delta W_1$ of 0.80 mass % or lower, or a ink composition comprising the surface-coated glass flake according to claim 5.

11. A cosmetic comprising a glass flake having a composition comprising, in terms of mass %:

$61 < SiO_2 \leqq 65$,
$8 \leqq Al_2O_3 < 12$,
$49 < (SiO_2 — Al_2O_3) \leqq 57$,
$3 \leqq MgO \leqq 3.5$,
$20 \leqq CaO \leqq 22.62$,
$0 < (Li_2O + Na_2O + K_2O) < 2$,
$0 \leqq TiO_2 \leqq 5$, and
$Li_2 < 0.36$, wherein a content ratio of $SiO_2$ to (MgO+CaO) is no less than 2.37, wherein a content of each of $B_2O_3$, F, ZnO, BaO, SrO, and $ZrO_2$ in the composition is less than 0.1 mass %, and wherein the glass flake has an index of acid resistance in terms of a mass reduction rate $\Delta W_1$ of 0.80 mass % or lower, or a cosmetic comprising the surface-coated glass flake according to claim 5.

12. The glass flake according to claim 1, wherein the composition is free from lanthanoid oxide.

13. The glass flake according to claim 1, wherein the range of $(Li_2O + Na_2O + K_2O)$ is $0.48 < (Li_2O + Na_2O + K_2O) < 2$.

14. The glass flake according to claim 1, wherein the range of $TiO_2$ is $0.25 < TiO_2 < 5$.

15. The glass flake according to claim 1, wherein the mass reduction rate $\Delta W_1$ is 0.50 mass % or lower.

16. The glass flake according to claim 1, wherein the glass flake has an index of alkali resistance in terms of a mass reduction rate $\Delta W_2$ of 3 mass % or lower.

17. The glass flake according to claim 1, wherein the glass flake has a working temperature no less than 1242° C.

18. The glass flake according to claim 1, wherein the glass flake has a $\Delta T$ of no greater than 48° C., where $\Delta T$ is obtained by subtracting a devitrification temperature from a working temperature of the glass flake.

* * * * *

UNITED STATES PATENT AND TRADEMARK OFFICE
CERTIFICATE OF CORRECTION

PATENT NO. : 8,383,531 B2
APPLICATION NO. : 11/793787
DATED : February 26, 2013
INVENTOR(S) : Fujiwara et al.

It is certified that error appears in the above-identified patent and that said Letters Patent is hereby corrected as shown below:

Title Page, Item 56, column 2, under "Foreign Patent Documents", line 6, delete "8/1993" and insert -- 1/1993 --.

Title Page, Item 57, column 2, under "Abstract", line 2, delete "$SiO_2<65$," and insert -- $SiO_2 \leq 65$, --.

Title Page, Item 57, column 2, under "Abstract", line 3, delete "$47<$" and insert -- $47 \leq$ --.

Specification, column 4, line 24, delete "$8 \leq Al_2O_3 \leq 12$," and insert -- $8 \leq Al_2O_3 < 12$, --.

Specification, column 4, line 25, delete "$10 \leq Al_2O_3 \leq 12$." and insert -- $10 \leq Al_2O_3 < 12$. --.

Specification, column 4, line 26, delete "$\leq SiO_2$—$Al_2O_3>$" and insert -- $<SiO_2$—$Al_2O_3>$ --.

Specification, column 5, line 50, delete "sate" and insert - -state- -.

Specification, column 9, line 50, delete "thereof," and insert - -thereof;- -.

Claims, column 15, line 51, in Claim 1, delete "$61<SiO_2 \leq 65$," and insert -- $61 \leq SiO_2 \leq 65$, --.

Claims, column 15, line 54, in Claim 1, delete "$3 \leq MgO \leq 3.5$," and insert -- $3 \leq MgO \leq 3.15$, --.

Claims, column 15, line 58, in Claim 1, delete "$Li_2<0.36$," and insert -- $Li_2O \leq 0.36$, --.

Signed and Sealed this
Eighth Day of October, 2013

Teresa Stanek Rea
*Deputy Director of the United States Patent and Trademark Office*

CERTIFICATE OF CORRECTION (continued)
U.S. Pat. No. 8,383,531 B2

Claims, column 15, line 59, in Claim 1, after "SiO$_2$" delete ",".

Claims, column 15, line 67, in Claim 2, delete "<55." and insert
-- $\leq 55$. --.

Claims, column 16, line 23, in Claim 8, delete "61<SiO$_2 \leq$65," and insert
-- $61 \leq SiO_2 \leq 65$, --.

Claims, column 16, line 26, in Claim 8, delete "3$\leq$MgO$\leq$3.5," and insert
-- $3 \leq MgO \leq 3.15$, --.

Claims, column 16, line 30, in Claim 8, delete "Li$_2$<0.36," and insert
-- $Li_2O \leq 0.36$, --.

Claims, column 16, line 41, in Claim 9, delete "61<SiO$_2 \leq$65," and insert
-- $61 \leq SiO_2 \leq 65$, --.

Claims, column 16, line 44, in Claim 9, delete "3$\leq$MgO$\leq$3.5," and insert
-- $3 \leq MgO \leq 3.15$, --.

Claims, column 16, line 48, in Claim 9, delete "Li$_2$<0.36," and insert
-- $Li_2O \leq 0.36$, --.

Claims, column 16, line 60, in Claim 10, delete "61<SiO$_2 \leq$65," and insert
-- $61 \leq SiO_2 \leq 65$, --.

Claims, column 16, line 63, in Claim 10, delete "3$\leq$MgO$\leq$3.5," and insert
-- $3 \leq MgO \leq 3.15$, --.

Claims, column 16, line 67, in Claim 10, delete "Li$_2$<0.36," and insert
-- $Li_2O \leq 0.36$, --.

Claims, column 17, line 1, in Claim 10, delete "SiO," and insert -- $SiO_2$ --.

Claims, column 17, line 12, in Claim 11, delete "61<SiO$_2 \leq$65," and insert
-- $61 \leq SiO_2 \leq 65$, --.

Claims, column 17, line 15, in Claim 11, delete "3$\leq$MgO$\leq$3.5," and insert
-- $3 \leq MgO \leq 3.15$, --.

Claims, column 17, line 19, in Claim 11, delete "Li$_2$<0.36," and insert
-- $Li_2O \leq 0.36$, --.

Claims, column 18, line 9, in Claim 13, delete "0.48<" and insert
-- $0.48 \leq$ --.

Claims, column 18, line 11, in Claim 14, delete "0.25<TiO$_2$<5." and insert
-- $0.25 \leq TiO_2 \leq 5$. --.

UNITED STATES PATENT AND TRADEMARK OFFICE
CERTIFICATE OF CORRECTION

PATENT NO. : 8,383,531 B2
APPLICATION NO. : 11/793787
DATED : February 26, 2013
INVENTOR(S) : Fujiwara et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 937 days.

Signed and Sealed this
First Day of September, 2015

Michelle K. Lee
*Director of the United States Patent and Trademark Office*